United States Patent [19]

Smith

[11] Patent Number: 5,403,323
[45] Date of Patent: Apr. 4, 1995

[54] METHOD AND APPARATUS FOR PHACO-EMULSIFICATION

[76] Inventor: Stewart G. Smith, 732 Nine Gates Rd., Yorklyn, Del. 19736

[21] Appl. No.: 59,953

[22] Filed: May 13, 1993

Related U.S. Application Data

[63] Continuation-in-part of Ser. No. 827,264, Jan. 29, 1992, abandoned.

[51] Int. Cl.⁶ .............................................. A61B 17/00
[52] U.S. Cl. .................................................... 606/107
[58] Field of Search ................. 606/1, 107, 108, 113, 606/205–209; 411/502; 128/898; 623/4, 6

[56] References Cited

U.S. PATENT DOCUMENTS

| | | | |
|---|---|---|---|
| 4,744,363 | 5/1988 | Hasson | 606/1 |
| 4,773,415 | 9/1988 | Tan | 606/107 |
| 5,007,913 | 4/1991 | Dulebohn et al. | 606/107 |
| 5,234,436 | 8/1993 | Eaton et al. | 606/107 |

Primary Examiner—Stephen C. Pellegrino
Assistant Examiner—Glenn Dawson
Attorney, Agent, or Firm—Herbert M. Wolfson

[57] ABSTRACT

A surgical method for removing tissue and other objects from the body of humans or animals, e.g. cataracts, blood clots, fatty deposits, etc. by disrupting them but minimizing the danger of piercing neighboring tissue through the use of a specially designed phaco-shield. This phaco-shield is inserted through the use of a specially designed shield guide.

3 Claims, 4 Drawing Sheets

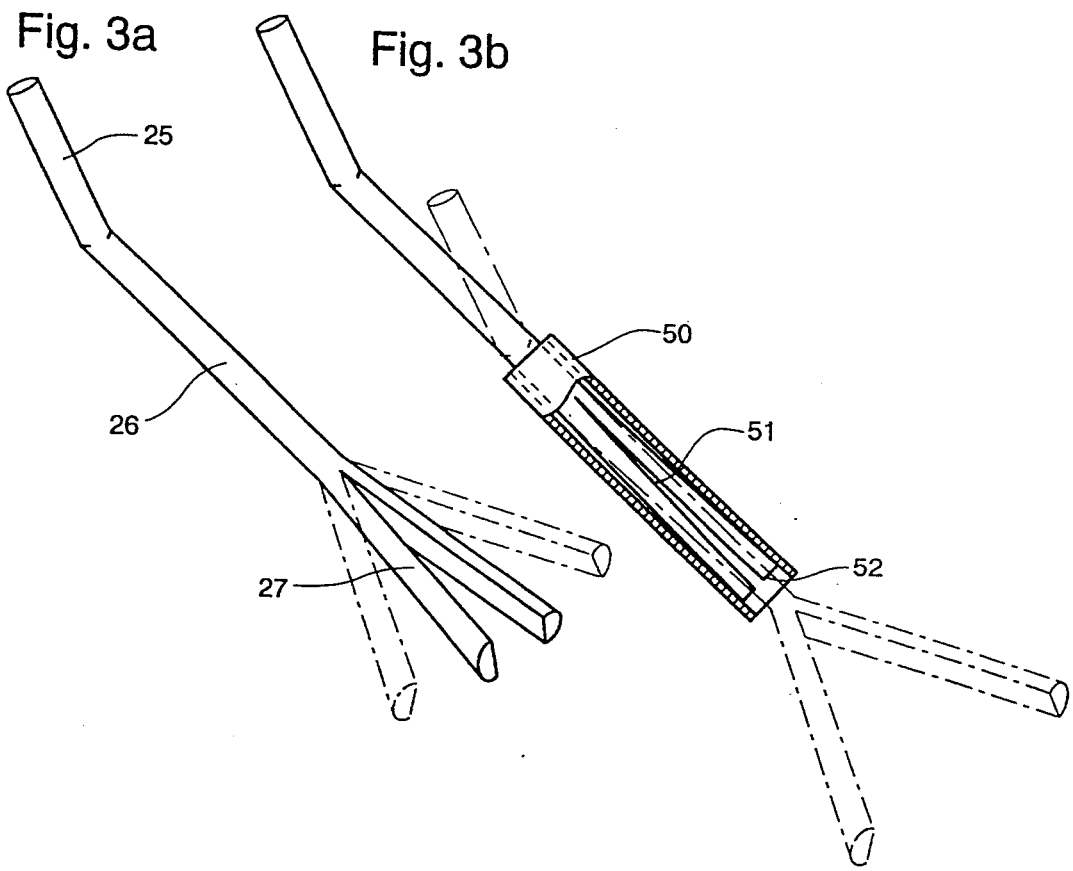
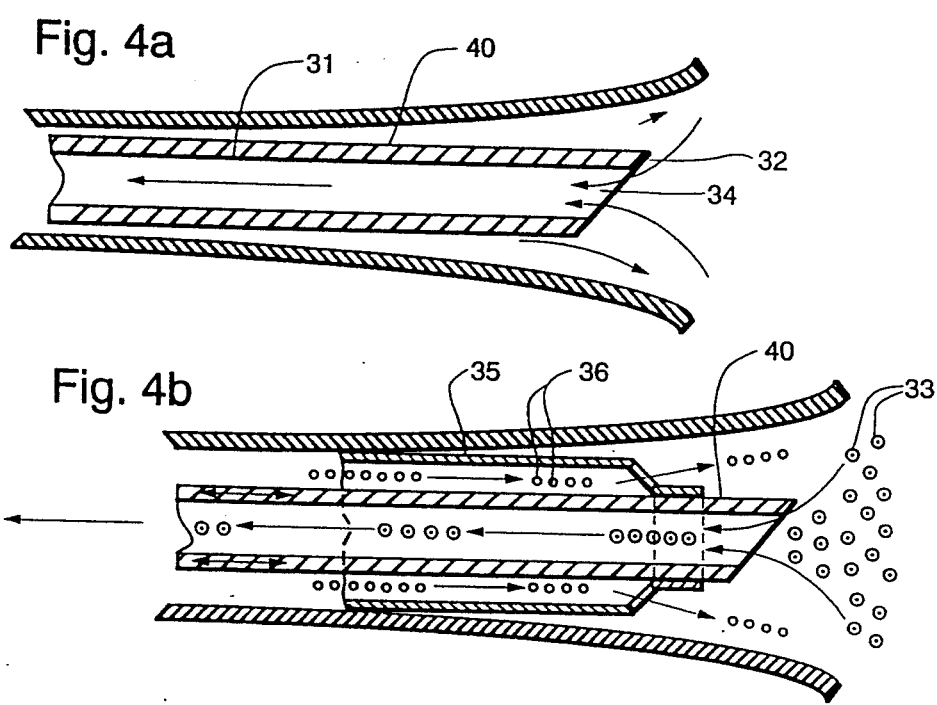

METHOD AND APPARATUS FOR PHACO-EMULSIFICATION

CROSS-REFERENCE TO RELATED INVENTION

This application is a continuation-in-part of U.S. application Ser. No. 07/827,264, filed Jan. 29, 1992, now abandoned.

FIELD OF THE INVENTION

This invention relates to cataract surgery and, more particularly, to the process of surgically removing the "diseased" lens or cataract more safely than heretofore. Specifically, the present invention relates to the use of a specially designed shield for performing the emulsification of the diseased lens (phaco-emulsification) and removing the "emulsion" in a safe, effective manner.

BACKGROUND OF THE INVENTION

As shown in FIG. 1 (the drawing showing the various parts of the eye), the lens 11 is perhaps the most critical element within the eye in providing vision for the human or animal. It is suspended behind the cornea 12, the anterior chamber 13 and the iris 14 by the zonular fibers which connect it with the ciliary body of muscles 15 around its periphery.

The lens is composed of a central region, the nucleus 16, surrounded by a softer outer region, the cortex 17. It is encapsulated in the lens capsule 18o which is a thin transparent membrane. The front part of the membrane is called the anterior capsule 20, and the rear part, the posterior capsule 21.

The function of the lens is to focus light rays upon the sensitive retina 19. To focus light from a distant object, the ciliary muscles 15 relax, thus tightening the zonular fibers and reducing the thickness of the lens to its minimal dimension. To focus light from a near object, the ciliary muscles 15 release the tension on the zonular fibers to increase the thickness of the lens, the lens assuming a near spherical shape. This change increases the lens refractive power to again obtain focusing of the light rays on the retina 19.

The lens consists of about 35% protein and 65% water. When the proteinaceous material hardens or becomes suffused with minerals, the lens becomes cloudy or opaque. A cloudy lens or an opaque, non-functional lens is a cataract. Most cataracts are not visible to the casual observer until they become dense enough to cause blindness.

Cataract surgery involves the removal of the "diseased" lens from the eye. Two principal procedures for lens extractions are practiced currently. Intracapsular surgery involves removal of the lens together with its surrounding capsule. Where the posterior capsule may be attached slightly to the vitreous membrane, extracapsular extraction of the lens is much preferred. Rupturing the vitreous membrane, a definite hazard in intracapsular surgery, has serious consequences, including vitreous loss, vitreous hemorrhage, retina detachment etc.

This invention relates to extracapsular extraction, the procedure considered the safest. However, even in extracapsular surgery where a probe or similar instrument is used to remove the lens, either as a complete lens or by first dissolving the cortex and then shattering or breaking down the nucleus into smaller bits or pieces and extracting the bits, the danger of the surgical instrument penetrating through the posterior capsule exists, even with the most careful surgeon. Vitreous loss or hemorrhage, retina detachment, etc. may result.

One of the currently used procedures for extracapsular extraction of cataracts is disclosed in U.S. Pat. No. 3,996,935. For this procedure, the anterior capsule is first ruptured and removed, followed by removal of the cortex and nucleus of the lens, leaving the posterior capsule intact.

The primary object of the present invention is to reduce the chances to substantially zero of penetrating the posterior capsule in performing cataract surgery while retaining the anterior capsule substantially intact.

A further object is to provide an instrument or device for achieving a successful procedure for removing unwanted objects from within the body without injuring neighboring body tissue.

A still further object is to provide a device that will not only almost insure success in cataract surgery, but provide an option to the surgeon for simplifying the procedure, using a smaller incision to retain the anterior capsule substantially intact and to use less complicated secondary instrumentation than had previously been necessary.

SUMMARY OF THE INVENTION

The objects of this invention are accomplished by employing an extracapsular procedure called phaco-emulsification. In general terms, this procedure involves the following steps: puncturing the anterior lens capsule; breaking up the lens; removing the broken bits of the lens while preventing the lens capsule from collapsing.

In practicing phaco-emulsification, a procedure of using a hollow tubular probe having a scalpel-like front edge, the probe being capable of drawing a vacuum through its hollow central portion. The sharp edge is used to break up or shatter the lens. The probe is surrounded by a cylindrical perforated tube, through which liquid is passed into the lens capsule. The liquid is used to emulsify the bits of lens so that they are withdrawn as part of an emulsion by the vacuum applied to the central portion of the probe. The liquid also serves to maintain the volume within the lens capsule at a constant level to prevent collapse of the capsular bag. Applying the proper vacuum in conjunction with the proper liquid feeding rate to prevent collapse of the capsule while removing the emulsion containing the bits of diseased lens requires extreme care and caution. Any collapse of the capsule against the sharp edge of the probe can puncture the capsule resulting in disaster. The improvement of the present invention will minimize and in most cases avoid the disaster possibility.

Specifically, the invention involves the insertion of a phaco-shield to partially surround the nucleus of the lens to be shattered, the shield having at least one flap sized and configured to extend beyond the leading sharp edge of the probe used for shattering. The shield is usually composed of two such flaps of biocompatible flexible (i.e. "floppy") plastic material attached to a base of a similar flexible material but usually thick enough to be rigid or self-supporting. When in place, the base extends over the cornea and sclera and the flaps extend partially over the upper and lower portions of the nucleus of the lens.

When the hollow probe is inserted, it is disposed within the phaco-shield. The probe is designed so that it never extends beyond the outer extremities of the "floppy" flaps of the shield. In fact, the probe is maintained sufficiently distant from the extremities of the flap so that at least one flap will fold or "flop" over the hollow opening of the probe to cut off the vacuum before the sharp edge of the probe can contact the posterior lens capsule. The flap, although "floppy", must be of sufficiently strong and resilient material to resist penetration by the tip of the probe.

Although a sharp, scalpel-like tip is illustrated as the leading edge of the probe, other designs are operable. Basically, the leading edge of the probe is adapted to disrupt or shatter tissue. When oscillated or moved into contact with the tissue, the leading edge will convert the tissue to particles or bits by shattering, breaking or abrading the unwanted cataract, tumor or foreign object, etc.

Besides protecting against penetration of the tip of the probe into the capsular bag, the shield is also capable of supporting the capsular bag physically and thus, preventing complete collapse of the capsular bag should the equilibrium be disturbed between the vacuum removing the emulsion containing the shattered bits of lens and the pressure of the replacement liquid being fed into the capsular bag.

The fact that the shield is capable of preventing complete collapse of the lens capsule provides the basis for another simplification in instrumentation for performing phaco-emulsification. The cylindrical perforated tube concentric with the hollow probe, as used currently, is no longer required. Without the danger of complete collapse, the liquid (usually a mild saline solution) can be fed into the lens capsule through a very small tubular entry at a constant relatively slow rate. Concern about maintaining flow rate to offset volume reduction due to withdrawing the emulsified lens particles under vacuum is avoided by the use of the phaco-shield of this invention.

The invention will be more clearly understood by referring to the drawings and the description which follow.

THE DRAWING

FIGS. 3a and 3b are views in perspective of inserter guides for guiding the flaps of the phaco-shield into position;

FIGS. 4a and 4b are schematic partial, cross-section views of shattering probes and the protective flaps of the phaco-shield.

DETAILED DESCRIPTION OF THE INVENTION

Figure 1:
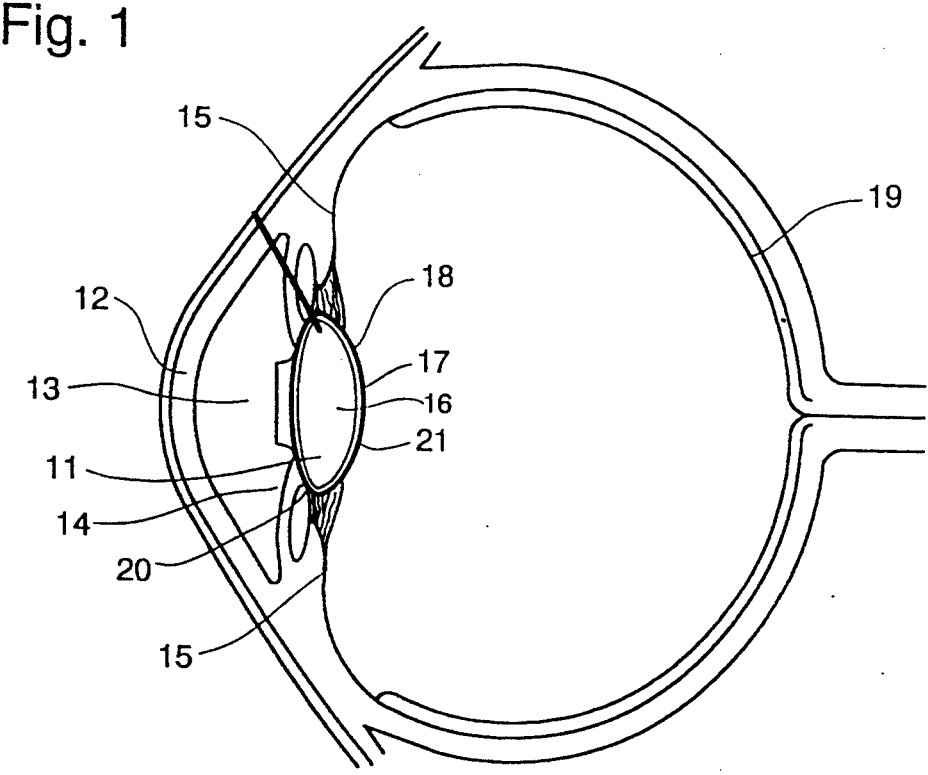
FIG. 1 is a cross-sectional view of the eye.
Figure 2:
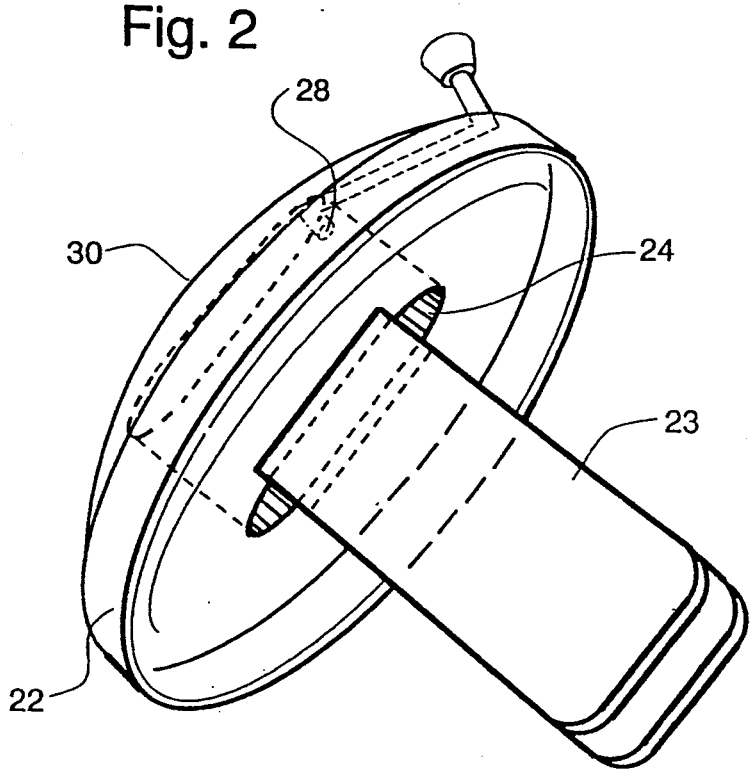
FIG. 2 is a view, in perspective, of a phaco-shield of the invention.

Referring to FIG. 2, a phaco-shield 30 is composed of two basic elements, the disk-shaped base 22 and at least one, preferably two protective flaps 23 connected directly to the base 22. Since the flaps 23 are adapted to protect a shattering probe. 40 inserted through the base 22, the base 22 will have an opening, preferably a "central" opening, 24 through which the probe 40 is inserted, The opening 24 also fits over the stiff wire-like "Y" inserter 26 that serves to guide the flaps 23 into position.

The phaco-shield 30 is manufactured from a polymeric material. The thickness of the base 22 must be such that it is self-supporting but sufficiently flexible to fit over, and conform to, the curved surface of the sclera or the cornea. The thickness is generally from 0.5 mm to 1.5 mm, preferably about 0.75 mm, depending upon the actual polymer and its molecular weight. The shape of the base 22 is elliptical, about 8 mm in length and about 4.5–5 mm in width. The central opening 24 in the base 22 is also elliptical, about 2.5–3 mm in length and about 1 mm in width.

The flaps 23, which may be molded integrally with base 22, as shown in FIG. 2, or bonded thereto, are usually thinner than the base. Although their thickness may be the same as the thickness of base 22, about 0.75 mm, they would be less dense but are preferably thinner, as thin as 0.25 mm. Their thickness and/or density is such that the flaps 23, are guidable by the inserter 26 but sufficiently floppy to cover the opening and, thus to shut or cut off the vacuum, in the shattering probe 31, should the probe tip get too close to the posterior capsule of the eye.

Preferably, the base 22 should have a second, tiny opening 28, through which fluid may be added during surgery to provide any additional liquid, besides body fluid, that may be necessary in the emulsification of the shattered bits of the diseased lens. As discussed earlier, the fluid may also serve to prevent collapse of the capsular bag in which the lens lies.

The polymeric material used in the manufacture of the shield may be any of those currently in use where biocompatibility is a requirement. Typically, such material comprise polysilicones, acrylic polymers, fluorocarbon polymers as well as olefinic polymer. The material should be clear, strong and flexible.

The wire-thin inserter 26 shown in FIG. 3a is composed of three integrated elements, a "handle" 25, a body or shank of the inserter 26 and the "Y" inserter end 27. It is manufactured as a single unit of spring metal, e.g. spring steel, and then split at the ends to provide the "Y" guiding portion, shown at 27. Since the split ends are thinner than the "handle" or the body, they will have greater flexibility and appear as the "V" portion of the "Y". When inserted into the eye through the thin (about 1 mm) and short (about 2.5–3 mm) incision to contact the opaque, hardened nucleus of the cataract and then rotated, the split ends 27 appear to separate around the nucleus to guide the "floppy" flaps 23 of the phaco-shield over the nucleus. A substantially rigid plastic that also has the capability of separating without breaking at one end in the manner shown for spring steel may also be used to make the inserter. Polypropylene or high density polyethylene are candidate polymers.

The shattering probe 40 shown in FIGS. 4a and 4b is composed of a cylindrical portion 31 and a sharp, scalpel—like forward edge 32. The metallic probe is adapted to vibrate at about 30,000 cycles per second enabling the forward edge 32, in the hands of a skilled surgeon, to gradually shatter the nucleus of the lens. The shattered bits 33, shown in FIG. 4b, are withdrawn in the form of a emulsion by applying a vacuum through the cylindrical opening 34, of the probe 40.

Variously shaped leading edges 32 for shattering are shown in a series of patents to Anton Banko. Among these are U.S. Pat. Nos. 3,996,935; 3,937,222; 3,618,594; 4,167,944; 3,945,375; 3,732,858; 4,117,843; and 4,368,734. Any of these edges can be adapted for use in utilizing the present invention; and the disclosures of these patents are hereby incorporated by reference into this specification.

In FIG. 4b, a probe having a concentric cylinder 35 with perforations 36 is disclosed. Liquid, fed into the capsular bag through the perforations, prevents collapse of the capsule and the liquid pressure offsets that of the vacuum being applied to withdraw the emulsified, shattered bits 33. Since the probe of FIG. 4b would require a larger opening for insertion, it is not preferred. As stated earlier, using the specially designed phacoshield of this invention serves to cut off the vacuum and prevent collapse of the lens capsule if the probe approaches the posterior capsule.

The steps of the surgical procedure, commonly called "phaco-emulsification", as practiced with the invented shield, are shown in FIGS. 5-9.

Figure 5:
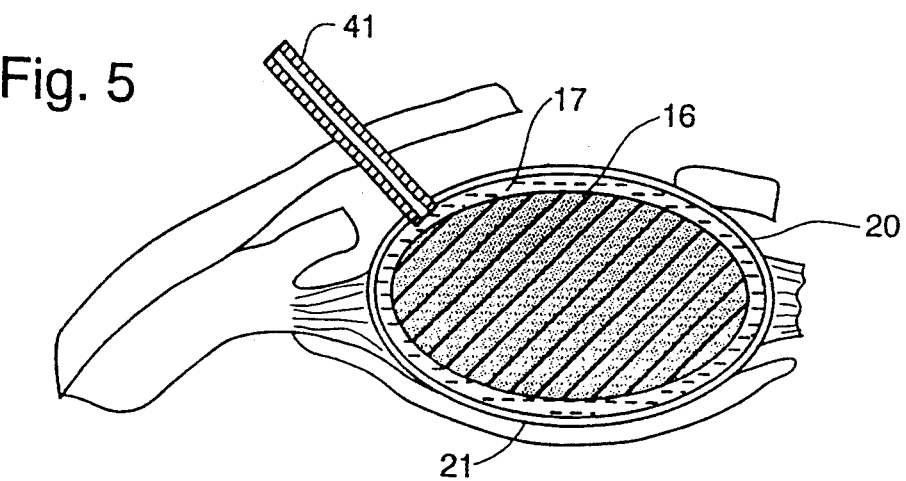
FIGS. 5–9 are schematic, partial, cross-sectional views of the eye with assorted instruments being used during the surgical procedure of shattering, emulsifying and removing the bits of shattered lens from the eye.

First, an incision of about 3 mm diameter is made in the anterior capsule of the eye. Through this incision, a 30 gauge cannula 41 is inserted for "hydro-dissection" as shown in FIG. 5. Fluid, usually a mild saline solution, is allowed to flow into the capsular area through the cannula 41 to separate the softer cortex 17 from the relatively hard nucleus 16 of the lens and to create a space between the lens and the posterior capsule.

Figure 6A:
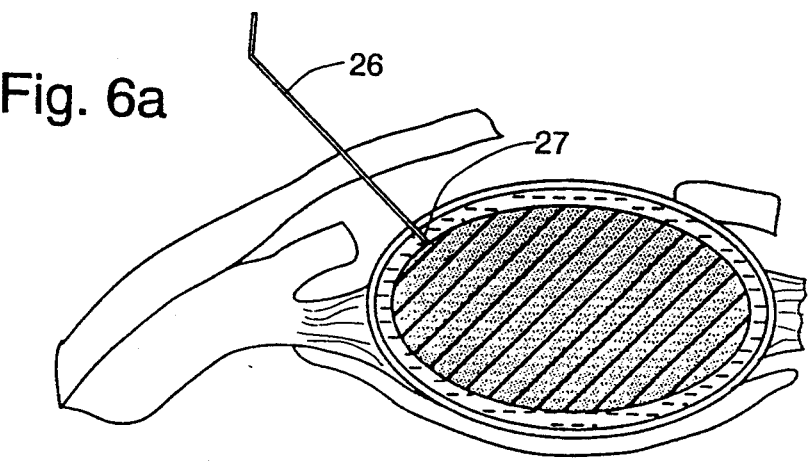
Figure 6B:
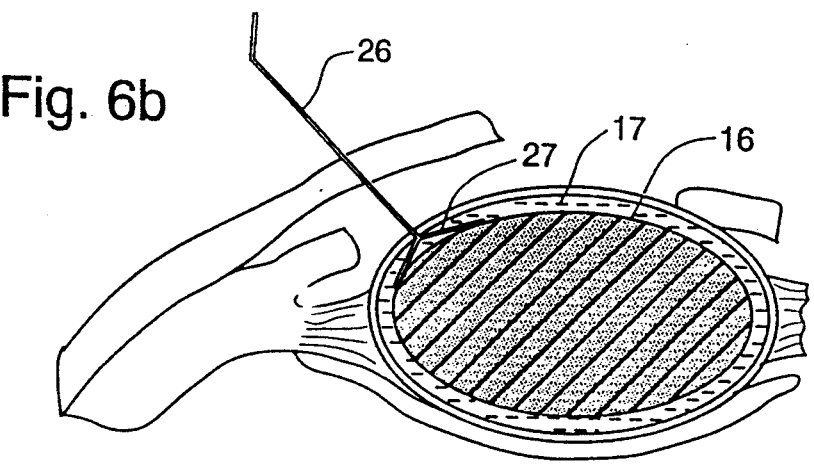

After the cannula 41 is withdrawn, the relatively stiff insert device or shield guide 26 is inserted through the same 3 mm incision, as shown in FIG. 6a. When first inserted, the guiding ends 27 of the inserter 26 are in a horizontal position to engage an edge of the nucleus 16. The inserter 26 is then rotated as in FIG. 6b to the vertical position which serves to spread the ends 27 so that they surround a portion of the nucleus.

Figure 7:
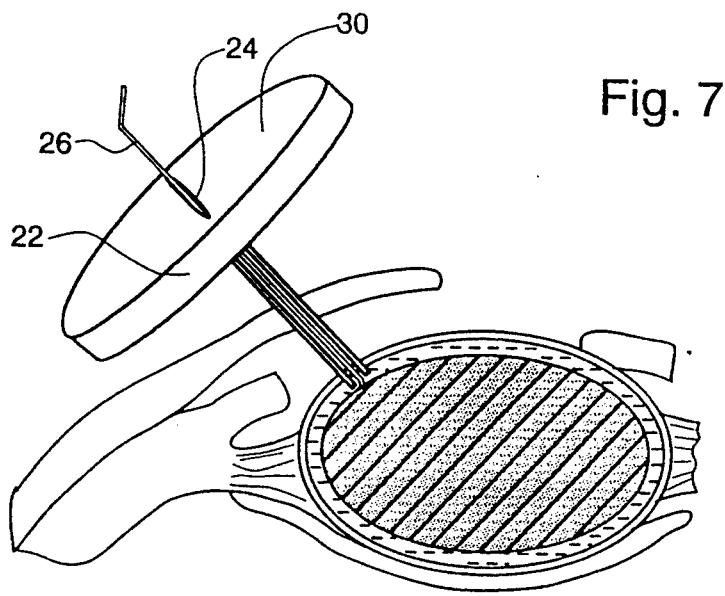

In FIG. 7, the phaco-shield of the invention 30 is shown being slid over the inserter 26. The central opening 24 in the base 22 of the shield 30 is adapted to be fitted over the inserter 26. The shield 30 is slid carefully along and over the insert device 26 so that the flaps 23 are 5 together and vertically oriented when they enter through the incision.

Figure 8:
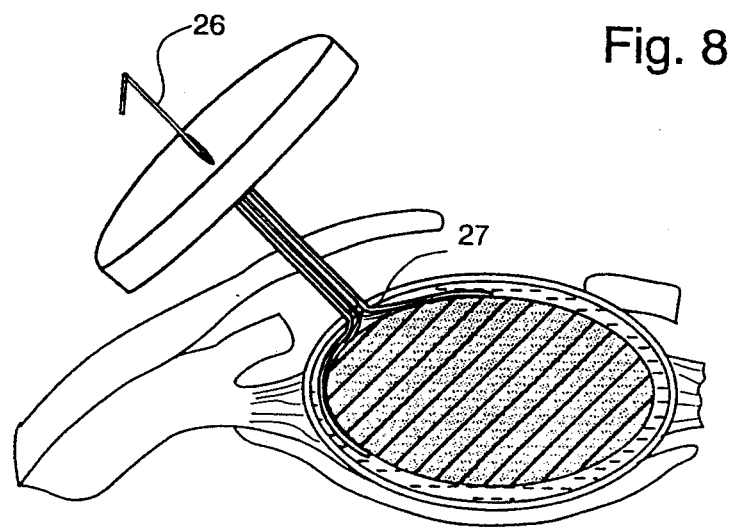

As shown in FIG. 8, the flaps 23 are deflected or guided by the previously rotated spread ends 27 of the inserter 26 to fill the space between the cortex and the 10 nucleus and to surround a portion of the nucleus of the diseased lens. When the flaps 23 have engaged about 50% of the surface of the nucleus to the satisfaction of the surgeon, and the base 22 is flush with the sclera or cornea, the insert device 26 is rotated to the horizontal position and removed.

Figure 9:
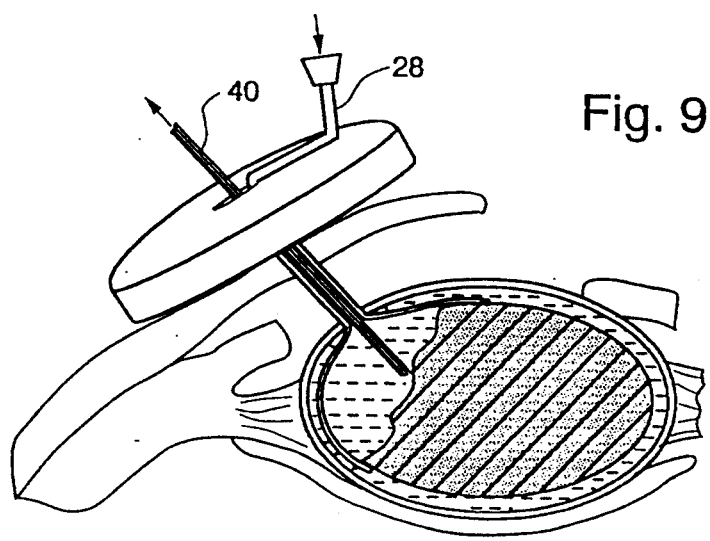

In FIG. 9, the shattering probe 40 is shown, having been inserted within the opening 24 of the shield 30 to replace the removed inserter 26. The small tube 28 has also been inserted through the opening in the base 22. As shown in this figure, about ⅓ of the nucleus has been shattered by the sharp leading edge 32 of the vibrating probe 40; and the shattered bits have been removed as an emulsion by the vacuum applied though the cylindrical opening in the probe 40. The emulsion of the shattered bits is formed with the 25 liquid that is allowed to flow by force of gravity into the capsule through the tube 28. The remaining nucleus is rotated with the probe tip to be shattered and then removed.

It should be understood that there are alternative methods of fitting the flaps 23 of the shield 30 over a portion of the nucleus. One alternative is to introduce both the shield 30 and the inserter 26 within the shield simultaneously; and rotate only the inserter 26 so that its spring steel ends 27 deflect outwardly to spread the flaps 23 over the nucleus.

An alternative inserting device is shown in FIG. 3b. It is composed of a hollow tube 50 with a solid rod 51 within it and having a split end 52 under tension such that when projected as shown by the arrow beyond the end of the tube 50 will spread apart, without being rotated, to form the "Y" inserter guide for the phacoshield. Projection of this inserting device 51 can be accomplished by using a spring-set trigger mechanism, not shown, that is operated by the surgeon.

Another possibility would be to have the split end 52 project beyond the end of tube 50 maintained under tension by a surrounding ring. By sliding the ring back (by an electromagnetic device), the split ends 52 will spread apart to form the "Y" inserter.

It is also possible to use the combination shown in FIG. 3b to accomplish the steps shown in FIGS. 6-9 in a single step. The hollow tube 50 can be considered equivalent to the probe 40 shown in FIG. 4a. Before the vacuum is applied, the solid rod 51 can be slid within the probe 40 and the phaco-shield 30 can be slid over the probe 40, After triggering the rod 51 to spread the ends 52, the rod is rotated and the phaco-shield 30 is slid into place. The flaps 23 are guided over the nucleus; the rod 51 is rotated and removed; the vibrating mechanism is attached to the rod 50 (probe 40) and the vacuum is applied through the space vacated by rod 51 (the inserting device).

Although the invented phaco-shield has been described for use in the removal of cataracts from the eye, it can be used in a variety of areas in the body where unwanted materials are found within, and in proximity to, delicate, vulnerable body tissue and a minimal incision is desirable. Such areas include, but should not be considered limited to:

1. Foreign objects within the vitreous humor of the eye to be removed without damaging the retina;
2. Fatty deposits or blood clots within arterial areas to be shattered without damaging the walls of the arteries;
3. Lumbar discs to be removed by emulsification. The shield can be modified to prevent injury to nerves or laterally to the spinal cord;
4. Polyps in the intestine; and
5. Stones in the kidney.

Thus, in its broadest sense, this invention relates to the use of a device having a substantially sharp leading edge that is manipulated by the surgeon to remove, usually by shattering, of an unwanted object, either foreign or developed naturally, e.g. cataracts, tumors, kidney stones, etc., that is disposed in proximity to body tissue that is vulnerable or can be damaged by the sharp edge. The invention provides protection for the vulnerable tissue by providing at least one plastic flap extending over the device in such manner that the flap will cover the sharp leading edge immediately prior to any contact of the edge with the vulnerable body tissue.

What is claimed:

1. A process for surgically removing a cataract from an eye which comprises the following steps:
   a) puncturing an anterior lens capsule of an eye to form an opening;
   b) separating a cortex from a hard nucleus of a cataractous lens of the eye;
   c) inserting a relatively stiff shield guide through the opening, the guide having a rod-like body with two wire-like separable ends extending into the eye;

d) rotating the shield guide in such manner that said separable ends separate and surround a portion of the nucleus;

e) sliding a phaco-shield over the rod-like body of said shield guide, the phaco-shield having a base adapted to fit closely over a portion of a sclera or cornea of the eye, a central opening in the base adapted to fit over the body of said shield and at least two flexible flaps adapted to fit through the opening in the anterior capsule and to slide over the body of said shield guide and over the separated ends of the shield guide to engage or partially surround a surface of the nucleus;

f) removing the shield guide through the opening in the base of the phaco-shield;

g) inserting a cylindrical probe through the opening in the base of the shield, the probe having a forward edge adapted to disrupt the nucleus upon contact.

h) introducing liquid into a capsular area of the eye while vibrating the probe to disrupt the nucleus into particles and to form an emulsion of the disrupted particles of the nucleus in the liquid;

i) applying a vacuum through a central opening of the cylindrical probe to withdraw the emulsion formed in step (h);

j) controlling the vacuum with the flexible flaps that engage the surface of the nucleus and surround the vibrating probe, at least one flap being adapted to cover the central opening of the probe when said flap contacts a surface of a posterior capsule of the eye.

2. A process for surgically removing a cataract from an eye which comprises the following steps:

a) puncturing a anterior lens capsule of the eye to form an opening;

b) inserting a cannula through the opening into a capsular area of the eye;

c) flowing a mild saline solution through the cannula to dissolve a cortex of a cataractous lens of the eye in the solution and, thus separating the cortex from a hard nucleus of the lens;

d) withdrawing the cannula and inserting a relatively stiff shield guide through the opening, the guide having a rod-like body with two wire-like separable ends extending into the eye;

e) rotating the shield guide in such manner that said separable ends separate and surround a portion of the nucleus;

f) sliding a phaco-shield over the rod-like body of said shield guide, the phaco-shield having a base adapted to fit closely over a portion of a sclera or cornea of the eye, a central opening in the base adapted to fit over the body of said shield guide and at least two flexible flaps adapted to fit through the opening in the anterior capsule and to slide over the body of said shield guide and over the separated ends of the shield guide to engage or partially surround a surface of the nucleus;

g) removing the shield guide through the opening in the base of the phaco-shield;

h) inserting a cylindrical probe through the opening in the base of the shield, the probe having a sharp, scalpel-like forward edge adapted to shatter the nucleus upon contact;

i) introducing liquid into the capsular area while vibrating the probe to shatter the nucleus into bits and to form an emulsion of the bits in the liquid;

j) applying a vacuum through a central opening of the cylindrical probe to withdraw the emulsion formed in step (i);

k) controlling the vacuum with the flexible flaps that engage the surface of the nucleus and surround the vibrating probe, at least one flap being 20 adapted to cover the central opening of the probe when said flap contacts a surface of a posterior capsule of the eye.

3. A process for surgically removing a cataract from an eye which comprises the following steps:

a) puncturing an anterior lens capsule of the eye to form an opening in a cornea or sclera of the eye;

b) separating a cortex from a hard nucleus of a cataractous lens of the eye;

c) guiding at least one flexible plastic flap through the opening in the anterior capsule and extending said flap over a surface of the nucleus;

d) inserting a cylindrical probe having a longitudinal passage through said opening, the probe also having a sharp leading edge adapted to disrupt the nucleus upon contact and the longitudinal passage adapted to flow liquid therethrough;

e) introducing liquid into a capsular area of the eye while vibrating and advancing said leading edge of the probe to disrupt the nucleus into particles and to form an emulsion of the disrupted particles of the nucleus in the liquid;

f) applying a vacuum through the longitudinal passage of the cylindrical probe to withdraw the emulsion formed in step (e);

g) deforming said flaps upon contact of said flap with the surface of the posterior capsule of the eye after said nucleus has been disrupted substantially completely to cover said leading edge of the probe thereby preventing said probe from damaging said posterior capsule.

* * * * *